United States Patent [19]
Svirklys

[11] 3,943,880
[45] Mar. 16, 1976

[54] ETCH TIMING DEVICE

[75] Inventor: Ferdinand M. Svirklys, Toronto, Canada

[73] Assignee: Dominion Al-Chrome Corporation, Toronto, Canada

[22] Filed: Sept. 30, 1974

[21] Appl. No.: 510,297

[52] U.S. Cl. ............................ 116/114 R; 23/253 C
[51] Int. Cl.² ........................................... G01N 31/00
[58] Field of Search .................... 116/114 R, 114.5; 23/230 C, 253 C; 73/73

[56] References Cited
UNITED STATES PATENTS

| | | | |
|---|---|---|---|
| 2,740,371 | 4/1956 | Nelson | 73/73 |
| 2,762,036 | 9/1956 | Triman | 23/253 C |
| 3,713,416 | 1/1973 | Volk | 116/114.5 |

Primary Examiner—S. Clement Swisher
Assistant Examiner—Denis E. Corr
Attorney, Agent, or Firm—Sim & McBurney

[57] ABSTRACT

An etch timing device for timing the etching of aluminum products and the like includes support members for supporting aluminum foil therebetween in a bath of etchant, the aluminum foil having dimensions corresponding to the quantity of aluminum to be etched in the bath. One of the support members is in a fixed position while the other is movable vertically relative to the first member. The movable support member is connected to the lower end of a rod which is slidably mounted in a hollow elongate body member mounted in association with the bath. The upper end of the rod extends above the height of the body member when the aluminum foil is supported and includes a visual indicator and stop means, typically a ring integrally formed with the upper end of the rod. When the ring moves downwardly upon dissolving of the aluminum foil, this provides a visual indication to the operator that the required etching has been completed.

5 Claims, 2 Drawing Figures

ETCH TIMING DEVICE

FIELD OF INVENTION

The present invention is directed to an etch timing device, more particularly to a timing device for the etching of metals.

BACKGROUND OF THE INVENTION

In the etching of metals, such as in the etching of aluminum products, the item such as an extrusion is immersed in a bath of an etchant such as sodium hydroxide solution in the case of aluminum. The quantity of metal to be removed is known and the time required usually is calculated assuming a known strength of etchant. However, this timing method is not satisfactory since its accuracy depends on a knowledge of the precise strength of the sodium hydroxide or other etchant solution, and errors may readily arise.

SUMMARY OF INVENTION

The present invention provides an etch timing device which indicates precisely that the desired quantity of metal has been etched irrespective of the concentration of the etchant solution. The present invention will be described hereinafter with particular reference to the etching of aluminum using a sodium hydroxide etchant solution, although it will be understood that other etchants may be used.

DESCRIPTION OF PREFERRED EMBODIMENTS

Figure 1:
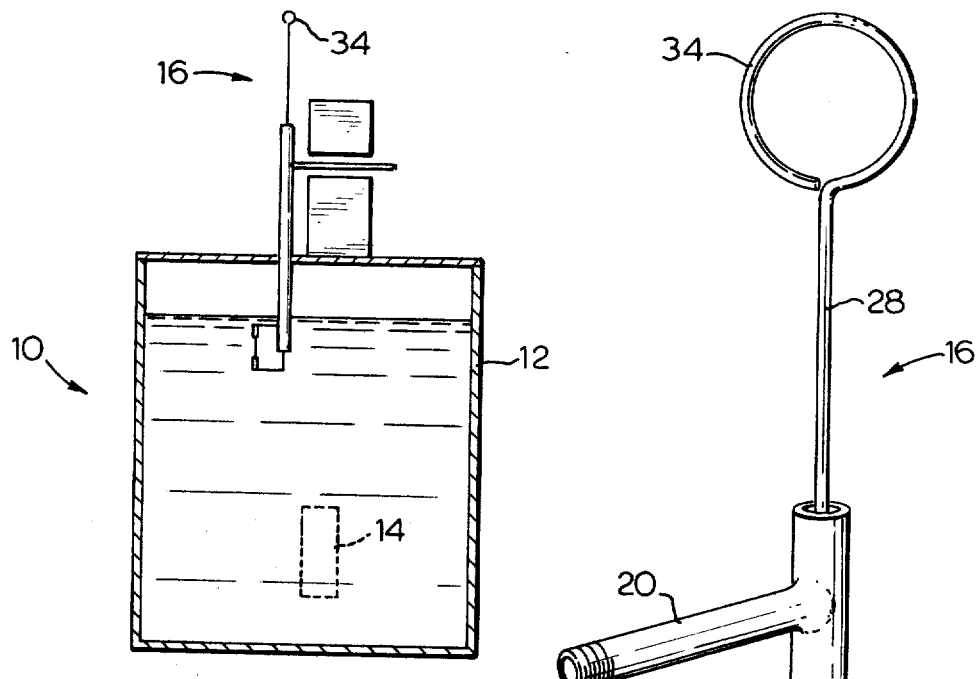
FIG. 1 illustrates an etch timing device in accordance with one embodiment of the invention in association with an etch tank.

Referring to the drawings, an etch tank 10 contains an aqueous solution of sodium hydroxide 12 of any desired concentration to etch an aluminum product 14. An etch timing device 16 is associated with the tank 10 and provides a visual warning when the required etching of the aluminum product 14 has been completed.

Figure 2:
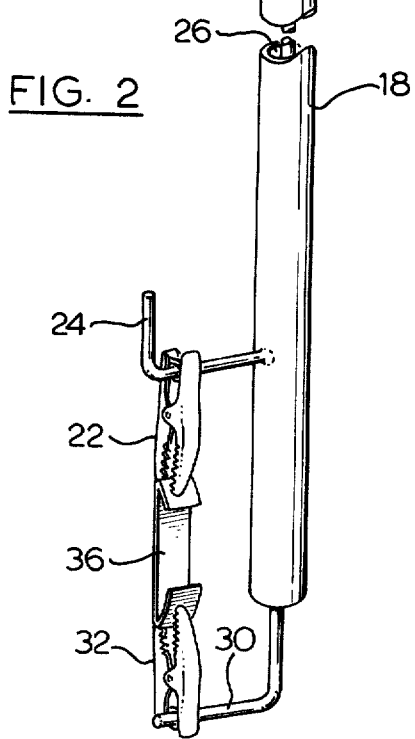
FIG. 2 is a detailed perspective view of the etch timing device of FIG. 1.

The etch timing device 16, illustrated in more detail in FIGS. 2 and 3, includes an elongate hollow body member 18. In the embodiment illustrated the body member 18 is of substantially square cross section although any other suitable cross sectional form may be used. A threaded bolt 20 is attached, in any convenient manner, to one face of the body member 18 for mounting of the timing device 16 on the tank 10. Any other suitable mounting means may be employed.

A clip 22, or other suitable support means, is mounted in fixed position relative to the body member 18. In the illustrated embodiment, the clip 22 is mounted on an arm 24 having a first part extending outwardly from one side of the body member 18 and a second part extending upwardly from the first part.

The clip 22 may be of any suitable form to grip a strip of aluminum in releasable manner and an alligator clip may be used.

The body member 18 has a bore 26 extending the length thereof. The bore 26 may have any convenient cross sectional shape, typically circular.

A rod-like movable member 28 is situated partially in the bore 26 and is slidable relative to the body member 18 in the bore 26. At its lower end, the movable member 28 terminates in an integral arm 30 extending transverse to the axis of movement of the movable member 28.

A clip 32, or other suitable support means, is fixedly mounted at the outer end of the arm 30 in opposed relation to the clip 22. The clip 32 may be of any suitable form to grip a strip of aluminum in releasable manner, typically an alligator clip.

The clips 22 and 32 cooperate to grip an aluminum foil element 36 therebetween. When the clips 22 and 32 are in the foil element 36 gripping position, a substantial length of the movable member 28 extends above the upper extremity of the body member 18 and is prevented from downward sliding movement by the gripping of the foil element 36 by the clips 22 and 32.

The body member 18, the movable member 28 and the clips 22 and 30 should be constructed of etchant-resistant material, suitably stainless steel or alkali- and acid-resistant plastic material.

At the upper end of the movable member 28 is ring 34 formed integrally with the remainder of the movable member 28.

OPERATION

In operation, an aluminum foil element 36 of dimensions such that it will be consumed by the etchant when the quantity of aluminum to be etched from the product 14 has been removed, is supported between the clips 22 and 32 and the lower portion of the device 16 is immersed in the etchant bath 12 along with the aluminum product 14. The projection of the ring 34 above the height of the body member 18 indicates to the operator the supporting of the aluminum foil element 36 between the clips 22 and 32.

When the aluminum foil element 36 has been consumed, corresponding to the time when the required amount of aluminum has been etched from the product 14, the movable element 28 slides downwardly under the force of gravity relative to the body member 18 until the ring 34 rests on the upper end of the body member 18. The movement of the ring 34 to this position indicates usually to the operator that the required etching of the product 14 has been completed and hence the product 14 should be removed from the tank 10.

The construction illustrated in the drawings provides a visual etch timing device. The visual signal may be supplemented, if desired, by an audible alarm which is actuated by the downward movement of the movable member 28 when the aluminum foil element 36 has been consumed.

Modifications are possible within the scope of the present invention.

What I claim as my invention is:

1. An etch timing device comprising
    first and second etchant-resistant support members adapted to cooperatively support a strip of etchant-consumable material therebetween in a bath of etchant,
    an elongate body member of etchant-resistant material adapted to be mounted in fixed position association with the bath of etchant, said body member having an axial bore formed therethrough, and
    a movable rod-like member of etchant-resistant material and extending through the axial bore in said body member and axially movable in sliding relation to said body member, one of said support members being mounted on said body member and the other of said support members being mounted on the lower end of said movable rod-like member, said support members being located external of the body member in straight line alignment and parallel to the axis of the bore in said body member, said rod-like member, when said first and second support members are in the strip-supporting position, extending beyond the upper extremity of said body member.

2. The timing device of claim 1 wherein said first and second support members each is an alligator clip, the clips being positioned with their jaws facing each other.

3. The timing device of claim 1 wherein a visual indicator means is provided at the upper end of said movable rod-like member.

4. The timing device of claim 1 including a ring integrally formed with the upper end of the movable rod-like member, said rod-like member being movable between a first position wherein said support members are adjacent one another and capable of supporting said strip of etchant-consumable material and said rod-like member extends beyond the upper extremity of said body member and a second position wherein said support members are spaced apart from each other and are incapable of supporting said strip and said ring engages said upper extremity of said body member.

5. The timing device of claim 4, wherein said first and second support members each is an alligator clip, the clips being positioned with their jaws facing each other.

* * * * *